(12) United States Patent
Kavermann

(10) Patent No.: US 11,717,630 B2
(45) Date of Patent: Aug. 8, 2023

(54) APPARATUS FOR USE IN A RESPIRATORY SUPPORT SYSTEM

(71) Applicant: Fisher & Paykel Healthcare Limited, Auckland (NZ)

(72) Inventor: Stephen William Kavermann, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 17/645,248

(22) Filed: Dec. 20, 2021

(65) Prior Publication Data
US 2022/0184336 A1    Jun. 16, 2022

Related U.S. Application Data

(63) Continuation of application No. 15/770,708, filed as application No. PCT/IB2016/056632 on Nov. 3, 2016, now Pat. No. 11,235,121.
(Continued)

(51) Int. Cl.
*A61M 16/08* (2006.01)
*A61M 16/01* (2006.01)
(Continued)

(52) U.S. Cl.
CPC ........ *A61M 16/0816* (2013.01); *A61M 16/01* (2013.01); *A61M 16/0875* (2013.01);
(Continued)

(58) Field of Classification Search
CPC .............. A61M 16/0816; A61M 16/01; A61M 16/0875; A61M 16/1095; A61M 16/16; F16L 37/138
See application file for complete search history.

(56) References Cited

U.S. PATENT DOCUMENTS 3,964,771 A     6/1976    Baudouin
4,610,468 A     9/1986    Wood
(Continued)

FOREIGN PATENT DOCUMENTS

EP    2612689 A1    7/2013
GB    2186652        8/1987
(Continued)

OTHER PUBLICATIONS

International Search Report; PCT/IB2016/056632; dated Jan. 3, 2017; 3 pages.

*Primary Examiner* — James M Hewitt, II
(74) *Attorney, Agent, or Firm* — Knobbe, Martens, Olson & Bear LLP

(57) ABSTRACT

A connector for a component of a medical breathing circuit. The connector comprises an inner body and an outer body. The outer body is configured to be slidable along the inner body between each of an inoperative orientation and an operative orientation with respect to the inner body. The outer body and the inner body are configured to be in engagement or in an operative association with each other when the outer body is provided in the operative orientation. The outer body and the inner body are disengaged from each other or in an inoperative association with each other when the outer body is provided in the inoperative orientation. At least one or each of a surface of the inner body or a surface of the outer body comprises of a surface relief feature(s) providing for a resistance to the outer body being moved from the inoperative orientation to the operative orientation.

15 Claims, 13 Drawing Sheets

Related U.S. Application Data

(60) Provisional application No. 62/252,149, filed on Nov. 6, 2015.

(51) Int. Cl.
*F16L 37/138* (2006.01)
*A61M 16/16* (2006.01)
*A61M 16/10* (2006.01)

(52) U.S. Cl.
CPC ........ *F16L 37/138* (2013.01); *A61M 16/1095* (2014.02); *A61M 16/16* (2013.01)

(56) References Cited

U.S. PATENT DOCUMENTS

| | | | |
|---|---|---|---|
| 4,846,167 A * | 7/1989 | Tibbals | F16L 35/00 |
| | | | 285/332 |
| 4,895,570 A * | 1/1990 | Larkin | A61M 39/1011 |
| | | | 604/905 |
| 5,029,904 A | 7/1991 | Hunt | |
| 5,242,431 A | 9/1993 | Kristiansen | |
| 5,297,819 A | 3/1994 | Harder | |
| 5,509,911 A * | 4/1996 | Cottone, Sr | A61M 39/1055 |
| | | | 604/905 |
| 6,302,447 B1 | 10/2001 | Lee | |
| 6,953,354 B2 | 10/2005 | Edirisuriya et al. | |
| 7,543,858 B1 * | 6/2009 | Wang | F16L 37/0982 |
| | | | 285/322 |
| 8,733,349 B2 | 5/2014 | Bath et al. | |
| 8,770,190 B2 | 7/2014 | Doherty et al. | |
| 11,235,121 B2 | 2/2022 | Kavermann | |
| 2004/0150223 A1* | 8/2004 | Campau | F16L 37/127 |
| | | | 285/308 |
| 2013/0167841 A1 | 7/2013 | Sheffer et al. | |
| 2014/0283827 A1 | 9/2014 | Flower et al. | |

FOREIGN PATENT DOCUMENTS

| | | |
|---|---|---|
| WO | WO 2005/065626 | 7/2005 |
| WO | WO 2014/129911 | 8/2014 |
| WO | WO 2015/089582 | 6/2015 |

\* cited by examiner

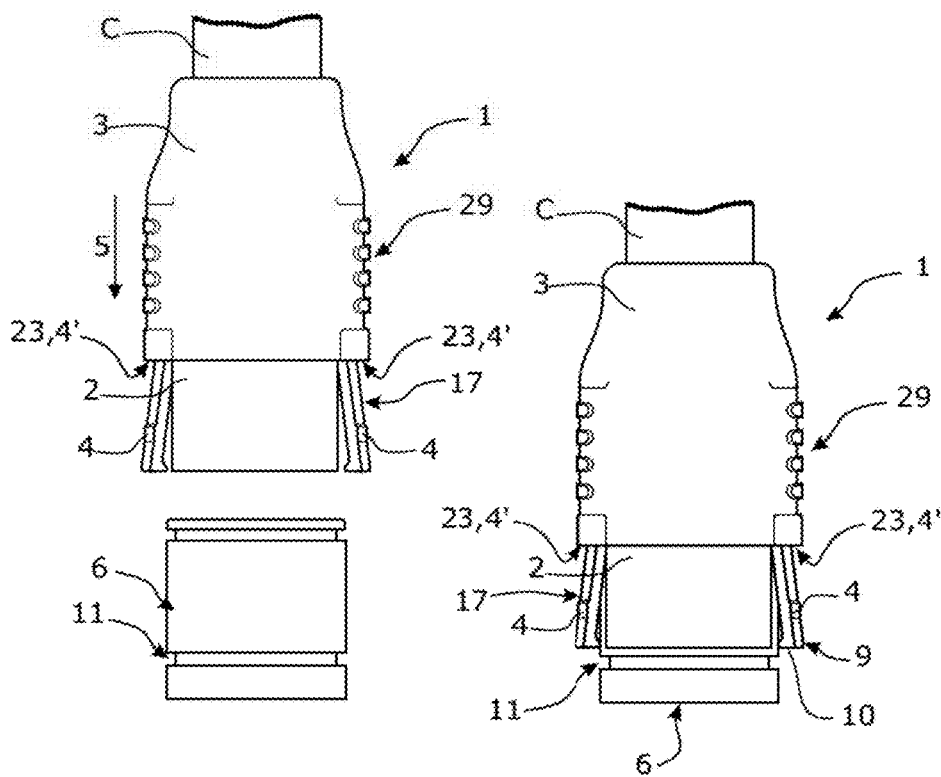
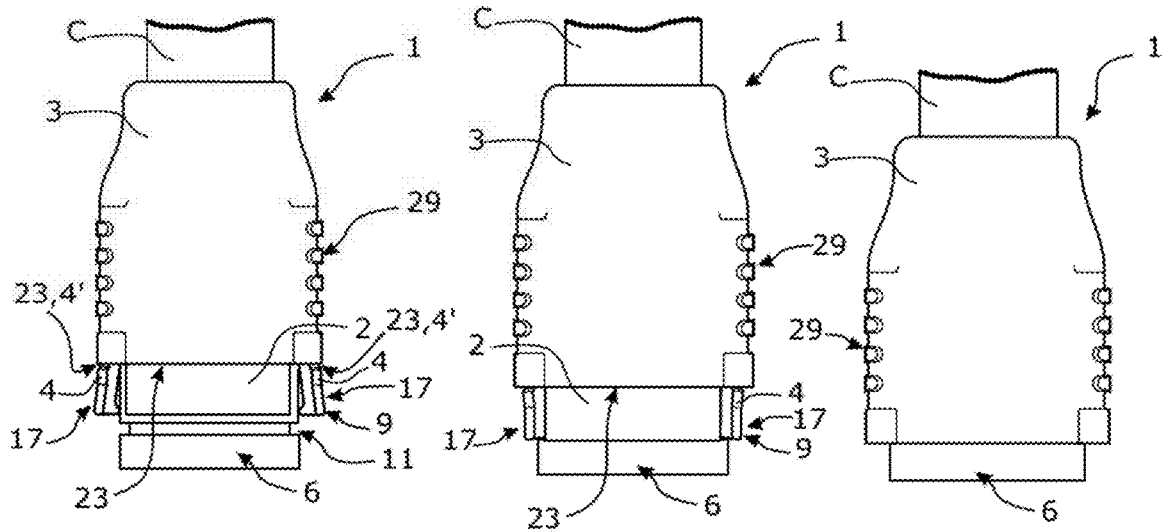
*FIGURE 6A*  *FIGURE 6B*
*FIGURE 6C*  *FIGURE 6D*  *FIGURE 6E*

APPARATUS FOR USE IN A RESPIRATORY SUPPORT SYSTEM

TECHNICAL FIELD

The present disclosure generally relates to a connector to be provided at a terminal end of a conduit. More particularly, the present disclosure relates to a releasable, yet secure, connector to be provided at the terminal end of a medical breathing conduit forming a part of a medical breathing circuit, for a releasable, yet secure, connection to be made between an end of the conduit with another device of the circuit (e.g. a humidifier or a flow generator or another conduit).

BACKGROUND ART

Alternative forms of connectors at the end of a conduit, such as a medical breathing conduit, for a connection to be made with a device forming a part of a breathing circuit, such as a medical breathing circuit, are desirable.

In particular, provision of such connectors which provide for a releasable yet secure connection provide for particular advantages. For example, a secure connection between the terminal end of a conduit and a device (such as a humidifier or a flow generator, such as a blower), or between two conduits, gives an operator (and the patient) reassurance of the delivery of a desired or intended respiratory therapy.

One such example of a more secure connector for the terminal end of a conduit is that disclosed by U.S. Pat. No. 6,953,354. Such a connector provides for a connector body surrounded by an external collar. The connector body is configured to fit with another connector of a device. The external collar is configured to move from an inoperative or 'open' position to an operative or 'closed' position in which, when in the operative or 'closed' position, the collar maintains the connector body in an engagement with portions of the other connector (i.e. of the device) to which it is being connected/attached. While the collar is in the operative or 'closed' position, the connector body is prevented from disconnection from the other connector (i.e. of the device) to which it is attached.

While recognising the type of connector provided for by U.S. Pat. No. 6,953,354 is particularly useful, enhancements or alternative features provide for still further connectors which operators may decide to choose. For example, some operators may inadvertently or prematurely move such an external collar into the operative or 'closed' position before the particular features of the connector body are correctly aligned or positioned relative to the other connector (i.e. of a device). As such, despite the collar being in the 'closed' position, a connection may not have been correctly made and no particular feedback (haptic, tactile or otherwise) may be given to the operator to otherwise assist with a correct connection being made or for even assisting with ensuring a correction is more likely to be made.

SUMMARY OF INVENTION

It is an object of certain embodiments disclosed herein to provide a connector for use in a medical breathing circuit or respiratory support system that will at least go some way towards improving on the above or which will at least provide the public or the medical profession with a useful choice. It is an alternative or additional object of certain embodiments disclosed herein to provide a connector for use at a terminal end of a medical breathing conduit that enables a releasable yet secure connection to be made with another component.

Humidified gases can be used to allow for comfortable gases delivery to a patient in some configurations. Humidity prevents the airways from drying out and hence can prevent or minimise damage to the airways and may also improve or assist with maintaining patient comfort when receiving a flow of gases being delivered to their airway(s).

In a first aspect, there is provided a connector for a component of a medical breathing circuit, the connector configured to connect with a second connector, the connector comprising: an inner body and an outer body, the outer body configured to be slidable along the inner body between each of an inoperative orientation and an operative orientation with respect to the inner body, the outer body and the inner body being in engagement or in an operative association with each other when the outer body is provided in the operative orientation, and the outer body and the inner body being disengaged from each other or in an inoperative association with each other when the outer body is provided in the inoperative orientation, wherein at least one or each of: (i) a surface of the inner body or (ii) a surface of the outer body comprise of a surface relief feature(s) providing for a resistance to the outer body being moved from the inoperative orientation to the operative orientation, and wherein the inner body further comprises at least one connection feature configured to retain the connector in connection with the second connector.

At least one or each of a surface of the inner body or a surface of the outer body may comprise a surface relief feature(s) that provide(s) for a first resistance to a force of displacement of the outer body being slidably moved from the inoperative orientation toward the operative orientation, and wherein the force of displacement required to overcome the first resistance is greater than a force of displacement subsequently required to complete the outer body being slidably moved to the operative orientation.

The connector may be configured such that a force required to engage the inner body with the second connector is less than a force required to move the outer body from the inoperative orientation to the operative orientation.

A force required to move the outer body from the inoperative orientation to the operative orientation when said inner body is in an engagement with the second connector, may be less than a force required to move the outer body from the inoperative orientation to the operative orientation when said inner body is out of an engagement with a connection feature of a second connector.

When said inner body of the connector is in an engagement with the second connector, a force required to move the outer body from the inoperative orientation to the operative orientation may be less than about 50 Newtons, optionally is about 30 Newtons. When said inner body of the connector is out of an engagement with the second connector, a force required to move the outer body from the inoperative orientation to the operative orientation may be greater than about 50 Newtons, optionally is about 100 Newtons.

The surface relief feature(s) may be provided about one or more of: an outer surface of the inner body; an inner surface of the outer body.

The surface relief feature(s) may be provided about an outer surface of the inner body.

The surface relief feature(s) may be provided about an inner surface of the outer body.

The surface relief feature(s) may extend(s) as a continuous or discontinuous formation or formations about a complete or a partial circumference of the inner body and/or of the outer body.

At least one of the surface relief features may be a protrusion configured to provide the resistance.

The at least one connection feature of said inner body of the connector may be one or more of:
- a raised tab or protrusion (optionally the raised tab extends substantially radially inwardly) to be received by a connection feature of the second connector when aligned for engagement (optionally to be received by a recess of the second connector),
- a recess configured for receipt of a connection feature of the second connector when aligned for engagement (optionally to be received by a recess of the second connector).

The connector and/or a second connector to which the connector is to be connected, or both, may comprise at least one connection feature configured to retain the connector relative to a second connector.

The outer body of the connector when in the operative orientation is configured to maintain or secure the at least one connection feature of the connector in a retained orientation relative to the second connector.

The inner body may comprises one or more latch members, optionally said one or more latch members is/are a deflectable portion of the inner body (optionally said latch member is/are deflectable substantially radially inwardly toward the second connector to which said latch member is to be engaged thereto when said outer body is moved into the operative orientation).

The at least one connection feature of said inner body may comprise a raised tab, optionally the raised tab extends substantially radially inwardly for receipt with a recess of a second connector.

The at least one connection feature of a said second connector may be a recess configured for receipt of a connection feature of a said connector (optionally a raised tab of said inner body).

A force required to move the outer body to the operative orientation when the at least one connection feature of the connector is aligned for an engagement into a retained orientation with connection features of the second connector may be less than a force required to move the outer body to the operative orientation when the at least one connection feature of the connector is out of alignment for an engagement into a retained orientation with connection features of the second connector.

A force required to move the outer body to the operative orientation when the at least one connection feature of the connector and the second connector are aligned for an engagement with each other into a retained orientation may be less than about 50 Newtons, optionally is less than about 30 Newtons.

A force required to move the outer body to the operative orientation when the connector and the second connector are attached to each other yet the at least one connection feature of the connector and the second connector are out of an alignment for an engagement with each other into a retained orientation may be greater than about 50 Newtons, optionally is about 100 Newtons.

The inner body comprises one or more latch members.

The one or more latch member(s) may be a deflectable portion of the inner body (optionally said latch member may be deflectable substantially radially inwardly toward a connection feature of a second connector to which said latch member is to be engaged thereto when said outer body is moved into the operative orientation).

An outside surface of one or each of said latch member(s) may comprise said surface relief feature(s).

At least one of said one or more latch members may comprise said at least one connection feature configured to retain the inner body relative to the second connector.

The connection feature of at least one of said one or more said latch members may comprise a raised tab, optionally said raised tab is configured to be received by a connection feature (e.g. a recess) of a said second connector when aligned for engagement (e.g. when aligned for engagement with the connection feature of a said second connector).

The connection feature of at least one of said one or more said latch members may comprise a recess, optionally said recess is configured to receive a connection feature (e.g. a raised tab) of a said second connector when aligned for engagement (e.g. when aligned for engagement with the connection feature of a said second connector).

The surface relief feature on an outside surface of a said latch member may be a protrusion or a raised profile that extends outwardly from said outside surface.

The protrusion or raised profile may be positioned or located substantially a predetermined length from an end of a said latch member, said end being the end of the latch member toward which said outer body is moved toward for the operative orientation.

The protrusion or raised profile may be positioned or located about 0 to about 15 mm from the end of the latch member, optionally is about 7 mm.

The surface relief feature may be a protrusion or raised profile, wherein said protrusion or raised profile has a ramped face, said ramped face inclining at an angle from the outer surface of the latch member to a radially outward point, and optionally being inclined in a direction toward said end of a latch member (optionally said end being the end of the latch member toward which said outer body is moved toward the operative orientation).

The ramped face may be inclined in a direction toward said end of a latch member (optionally said end being the end of the latch member toward which said outer body is moved toward for the operative orientation), the angle of said ramped face being:
  i. an angle of about 40° to about 60° (degrees), optionally is at an angle of about 45°, optionally is at an angle of less than about 90°, when said angle is measured with respect to the outer surface of the latch member,
  ii. an angle of about 40° to about 60° (degrees), optionally is at an angle of about 45°, optionally is at an angle of less than about 90°, when said angle is measured from an axis perpendicular to the outer surface of a second connector.

The surface relief feature on the outside surface of a said latch member may interferes with, or may be contacted by, a surface of the outer body when said outer body is moved in a direction from the inoperative orientation to the operative orientation.

The surface of the outer body may comprise a leading edge or face, the leading edge or face being at an end of the outer body that makes initial interference or contact with a said surface relief feature provided on the outside surface of said latch member or the inner body when said outer body is moved in a direction from the inoperative orientation to the operative orientation.

An inside surface of the outer body may comprise one or more of said surface relief features, a leading edge or face of which are configured to make an initial interference or contact with a said surface relief feature provided on an outside surface of said inner body or a said latch member when said outer body is moved in a direction from the inoperative orientation to the operative orientation.

The one or more surface relief features on the inside surface of the outer body may be a protrusion or a raised profile that extends inwardly from the inside surface.

The protrusion or raised profile of the outer body may have a ramped face, said ramped face inclining at an angle from the inner surface of the outer body to a radially inward point, and optionally being inclined in a direction away the leading edge or face of the outer body.

The ramped face may be inclined in a direction toward said end of the outer body (optionally said end being the end of the outer body toward which said outer body is moved toward for the inoperative orientation), the angle of said ramped face being:
  i. an angle of about 40° to about 60° (degrees), optionally is at an angle of about 45°, optionally is at an angle of less than about 90°, when said angle is measured with respect to the inner surface of the outer body,
  ii. an angle of about 40° to about 60° (degrees), optionally is at an angle of about 45°, optionally is at an angle of less than about 90°, when said angle is measured from an axis perpendicular to the outer surface of a second connector.

In the inoperative orientation, the outer body may be out of an engagement or association with surface relief features of the inner body.

In the operative orientation, the outer body may be in an engagement or association with surface relief features of the inner body.

In the operative orientation, the outer body may be configured to urge one or more connection features (or one or more latch members) of the inner body inwardly toward a latched configuration with the second connector.

In the operative condition, the outer body may maintain or secure one or more connection features (or one or more latch members) of the inner body in a retained orientation relative to the second connector.

The inner body may define internally a lumen or gas flow passage for the transport of gas.

When the connector is connected in a retained orientation with a second connector, a pneumatic connection may be made between said connector and said second connector.

The at least one connection feature of a said second connector may be one or more of:
  a raised tab or protrusion to be received by a connection feature of the connector when aligned for engagement (optionally to be received by a recess of the connector),
  a recess configured for receipt of a connection feature of the connector when aligned for engagement (optionally to be received by a recess of the connector).

A force required to move the outer body to the operative orientation when the at least one connection feature of the connector is aligned for an engagement into a retained orientation with connection features of the second connector may be less than a force required to move the outer body to the operative orientation when the at least one connection feature of the connector is out of alignment for an engagement into a retained orientation with connection features of the second connector.

A force required to move the outer body to the operative orientation when the at least one connection feature of the connector and at least one connection feature of the second connector are aligned for an engagement with each other into a retained orientation may be less than about 50 Newtons, optionally is less than about 30 Newtons.

A force required to move the outer body to the operative orientation when the first connector and the second connector are attached to each other yet the at least one connection feature of the first connector and at least one connection feature of the second connector are out of an alignment for an engagement with each other into a retained orientation may be greater than about 50 Newtons, optionally is about 100 Newtons.

The inner body of the first connector may comprise one or more latch members, optionally said latch member is a deflectable portion of the inner body (optionally said latch member being deflectable substantially radially inwardly toward a connection feature of the second connector to which said latch member is to be engaged thereto when said outer body is moved into the operative orientation).

The inner body of the connecter may be connectable or attachable to a conduit, optionally the conduit may be a medical breathing tube.

The inner body may provide for a lumen to provide a gases transport pathway to the lumen of the conduit.

When in the inoperative orientation, the outer body may be in a retracted position relative to the inner body, optionally in the inoperative or retracted portion the outer body is allowed to slide over the outside of the conduit which is attached to the lumen of the inner body.

In a second aspect, there is provided connector assembly comprising the connector as defined by the first aspect and any of the configurations as described above and a second connector to which the defined connector is connectable.

The defined connector may be configured as a female connector and the second connector is configured as a male connector.

In a third aspect, there is provided a connector for a component of a medical breathing circuit, the connector comprising: a female connector portion, wherein the female connector portion comprises an inner body and an outer body, the outer body configured to be in a slidable relationship with the inner body, and wherein at least one, or both of, an outside surface of the inner body and an inside surface of the outer body, comprise a surface relief feature(s).

The connector may be as defined by the first aspect and any of the configurations as described above.

The connector may be adapted for connection to the male end of a second connector.

The inner body may be an inner connector body.

The outer body may be an outer collar body.

In a fourth aspect there is provided a connector assembly comprising:
  a first connector of the first, second or third aspects, and
  a second connector comprising at least one connection feature, the at least one connection feature of the first connector being configured to engage with the at least one connection feature of the second connector to retain the first connector in connection with the second connector.

The outer body when in the operative orientation may be configured to maintain or secure the at least one connection feature in a retained orientation relative to a said second connector.

The at least one connection feature of a said second connector may be one or more of:
  a raised tab or protrusion to be received by a connection feature of the first said connector when aligned for engagement (optionally to be received by a recess of the first connector), a recess configured for receipt of a connection feature of the first connector when aligned for engagement (optionally to be received by a recess of the first connector).

A force required to move the outer body to the operative orientation when the at least one connection feature of the first connector is aligned for an engagement into a retained orientation with connection features of the second connector may be less than a force required to move the outer body to the operative orientation when the at least one connection feature of the first connector is out of alignment for an engagement into a retained orientation with connection features of the second connector.

A force required to move the outer body to the operative orientation when the at least one connection feature of the first connector and at least one connection feature of the second connector are aligned for an engagement with each other into a retained orientation may be less than about 50 Newtons, optionally is less than about 30 Newtons.

A force required to move the outer body to the operative orientation when the first connector and the second connector are attached to each other yet the at least one connection feature of the first connector and at least one connection feature of the second connector are out of an alignment for an engagement with each other into a retained orientation may be greater than about 50 Newtons, optionally is about 100 Newtons.

The inner body of the first connector may comprise one or more latch members, optionally said latch member is a deflectable portion of the inner body (optionally said latch member being deflectable substantially radially inwardly toward a connection feature of the second connector to which said latch member is to be engaged thereto when said outer body is moved into the operative orientation).

According to the various aspects or configurations above, or as described herein, when in the inoperative condition, the outer body does not maintain or secure one or more connection features (or one or more latch members) of the inner body in a retained orientation relative to a second connector.

It should be understood that alternative embodiments may comprise any or all combinations of two or more of the parts, elements or features illustrated, described or referred to in this specification.

BRIEF DESCRIPTION OF THE DRAWINGS

Specific embodiments and modifications thereof will become apparent to those skilled in the art from the detailed description herein having reference to the figures that follow, of which:

FIG. 4 also illustrates how in various embodiments latch members having an inwardly orientated or directed raised tab can have the raised tab (or barb or hook type configuration) moved into connection with a recess of another connector.

FIGS. 6A-E show a sequence of an embodiment of a connector being put into connection with a second connector; in particular FIG. 6A shows a connector with an outer body in an inoperative orientation with respect to an inner body the connector being wholly separate from another connector to which a connection is to be made. FIG. 6B shows the connector in a first stage of connection in which a second connector has been inserted into the female end of the inner body of the connector; FIG. 6C shows the outer body of the connector moved into a position of encountering a resistance with a surface relief feature of an inner body; FIG. 6D shows the outer body and the inner body having been moved together (e.g. in tandem) to be slid along the shaft or shank of the second connector for bringing connection features of the connector into receipt with commensurate connection features of the second connector; and, FIG. 6E shows the connector in correct connection with the second connector with the outer body in the operative orientation with respect to the inner body.

DETAILED DESCRIPTION OF SPECIFIC EMBODIMENTS

Figure 1:
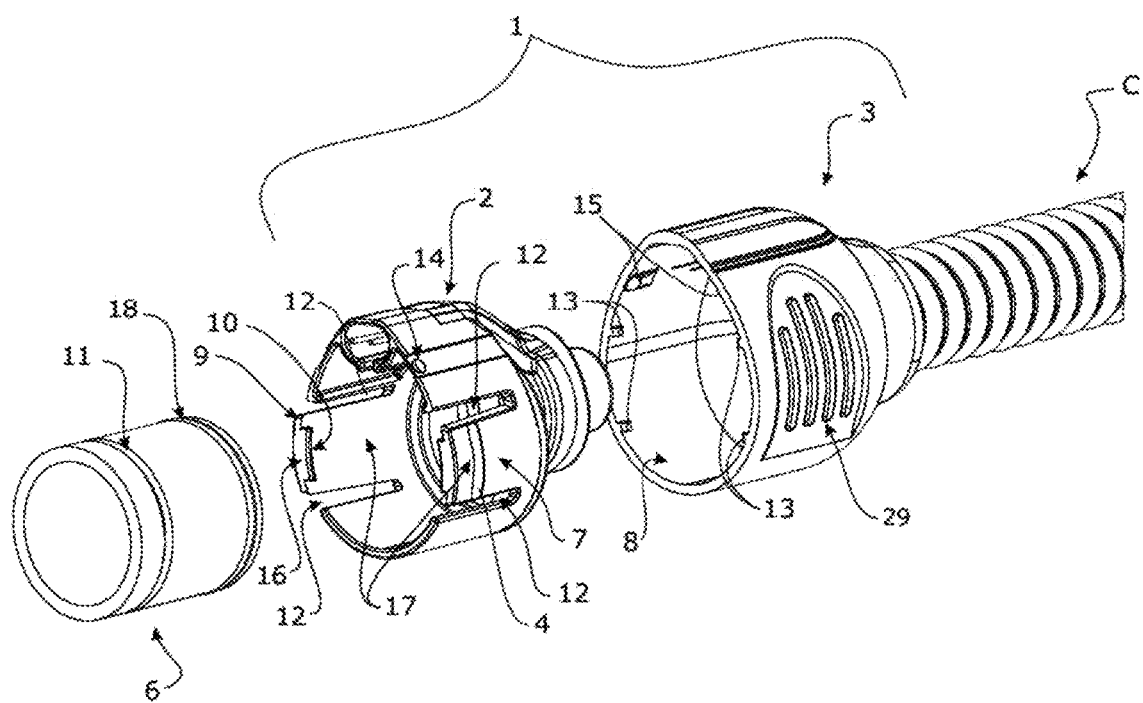
FIGS. 1 and 2 illustrate exploded views of a connector of an embodiment of this disclosure, as well as an exemplification of a second connector to which a connection may be made.

The connector of the present disclosure provides for an arrangement which is configured to go at least some way towards improving the likelihood of a user making the correct and a complete connection with a second connector.

The connector of the present disclosure has particular applicability to its use as a female connector which is adapted for connection to a male part of a second connector.

The connector may be provided as a first connector for connection with a second connector as part of a connector assembly.

In some embodiments, the connector or second connector is provided as a part of a flow generator, humidifier or other device which provides conditioned air or other gases to a user. In addition, or alternatively, the connector or second connector may be provided as part of a component of a medical breathing circuit (for example as a connector on an end of a breathing conduit).

In some embodiments, the connector or second connector may be provided as part of a conduit associated with a patient interface such as a mask (whether as a full face-type mask or otherwise), or nasal cannula, these being either of a sealing or non-sealing type. In some embodiments, the connector may be provided for connecting a conduit to a patient interface (such as a nasal cannula or mask), or a conduit of a patient interface.

With reference to the accompanying figures, there is provided a connector 1 for a component (such as a medical breathing conduit) of a medical breathing circuit. Such a connector 1 comprises of an inner body 2 and an outer body 3. The outer body 3 is configured to be slidable along the inner body 2 between each of an inoperative orientation (for example, such as that shown by FIGS. 6A, 6B) and an operative orientation (for example, such as that shown by FIG. 6E) with respect to the inner body 2. The outer body 3 and the inner body 2 being in engagement or in the operative association with each other when the outer body 3 is provided in the operative orientation; and, the outer body 3 and the inner body 2 being disengaged from each other or in the inoperative association with each other when the outer body 3 is provided in the inoperative orientation. The inner body 2 further comprises at least one connection feature 9 configured to retain the connector 1 upon a second connector 6.

According to these features, at least one or each of a surface of the inner body 2 or a surface of the outer body 3 may comprise of a surface relief feature(s) 4 providing for a resistance to the outer body 3 being moved (or slid) from the inoperative orientation to the operative orientation.

FIG. 1 illustrates the connector 1 in an exploded arrangement, in addition to a second connector 6 as one embodiment of another connector to which a connection may be made. A second connector 6 may optionally comprise a recess to house or receive a sealing member 18 such as an o-ring. The sealing member, such as an o-ring, may facilitate sealing for a pneumatic connection to be formed between the connector 1 and a second connector 6, although it will be appreciated a pneumatic connection may be formed between the connector 1 and a second connector irrespective of whether a sealing member 18 is particularly used or not, a sealing member 18 may however improve sealing.

Figure 2:
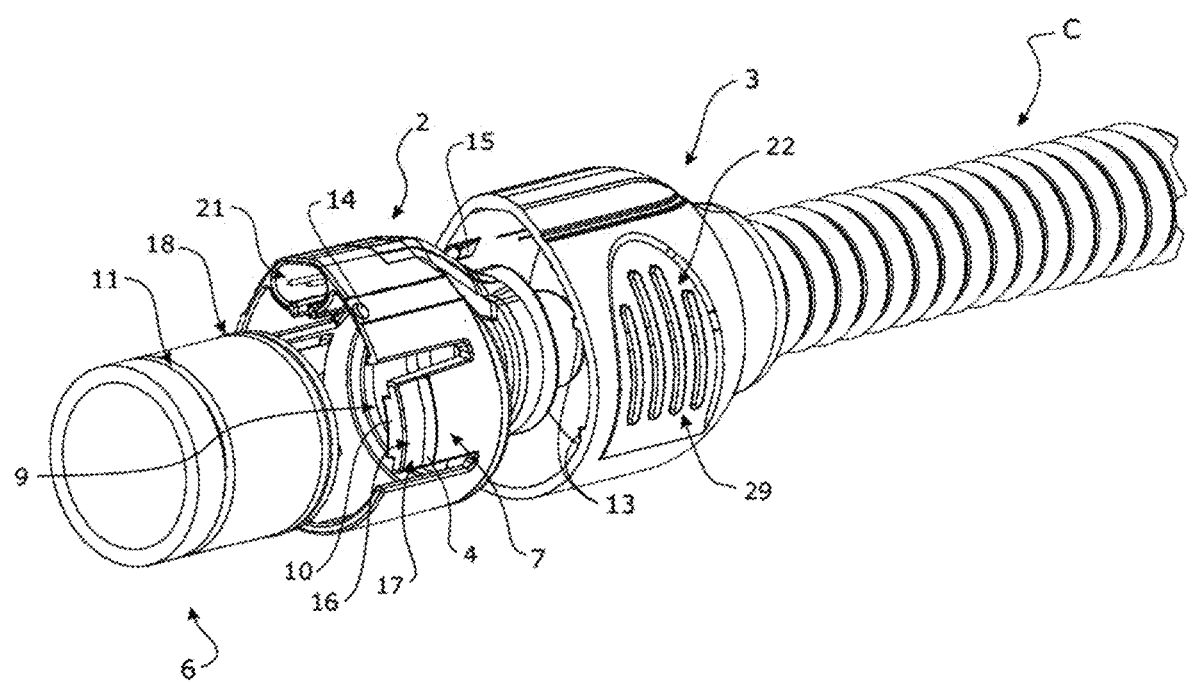

FIG. 2 illustrates the connector 1 as the outer body 3 and the inner body 2 are in the process of being assembled (though still partially separated from each other), with an optional second connector 6 to which a connection by the inner body 2 may be made.

Figure 3:
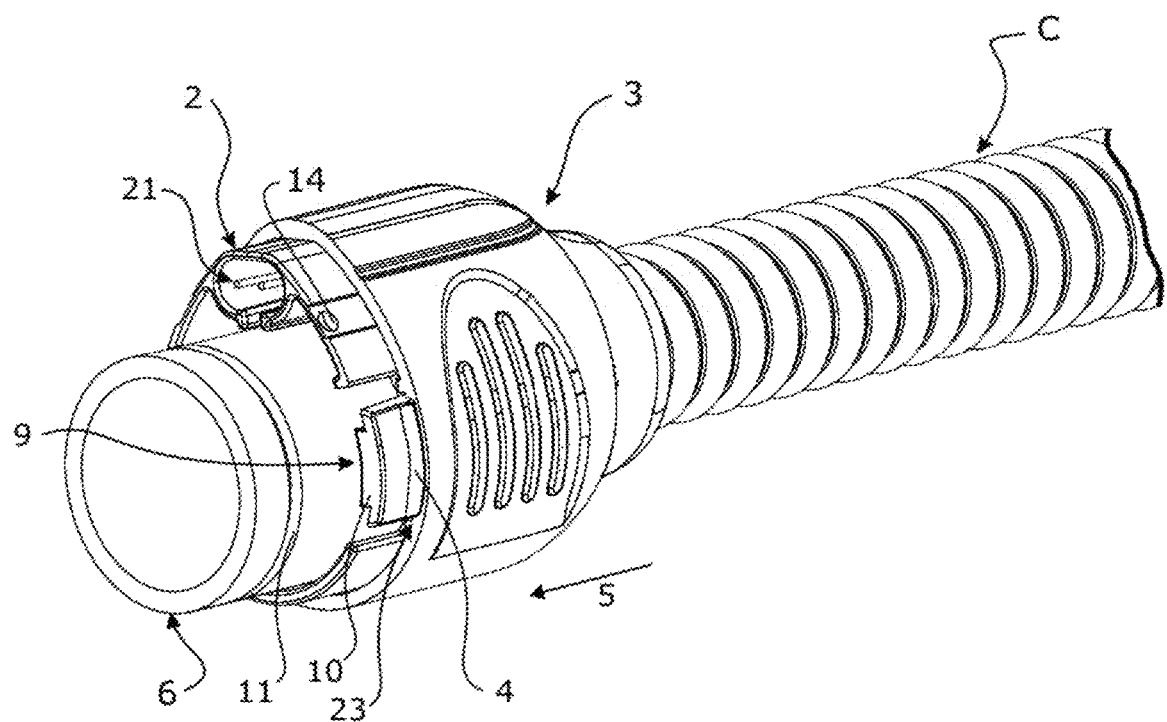
FIG. 3 illustrates an embodiment of a connector, in particular where an outer body of the connector has been slid along an inner body of the connector, and the outer body first realises a resistance to further sliding along the inner body.

FIG. 3 illustrates the outer body 3 having been slid or translated along the inner body 2 and having reached a point where a resistance to the sliding or movement along the inner body has been made. For example, a surface relief feature 4 is providing a resistance against an end surface or face or leading edge 23 of the outer body 3. Also shown (and for example as shown in FIG. 1) is a guide path 12 and a guide path locator 13 for assisting with a determined direction or orientation for travel of the outer body 3 with respect to the inner body 2.

A guide path 12 and a guide path locator 13 may be of use when the inner body is substantially circular when viewed in cross-section to the axial or longitudinal direction of the connector. In such a situation, the guide path and guide path locator can be utilised to prevent the outer body from rotating about the inner body. In some embodiments, for ease of use or user operability, there may be a desire to avoid a rotation of the outer body relative to the inner body.

The guide path 12 can simultaneously act as an effective slot or cut-out of the inner body, thereby allowing the connection features 9 of the inner body or the latch members 17 of the inner body comprising the connection features 9, to be able to be moved independently of the remainder of the inner body. In this manner the connection features 9 or latch members 17 may be deflected inwardly as the outer body is brought to bear upon a surface relief feature of the inner body or upon the connection features 9 or latch members 17 themselves.

Figure 4:
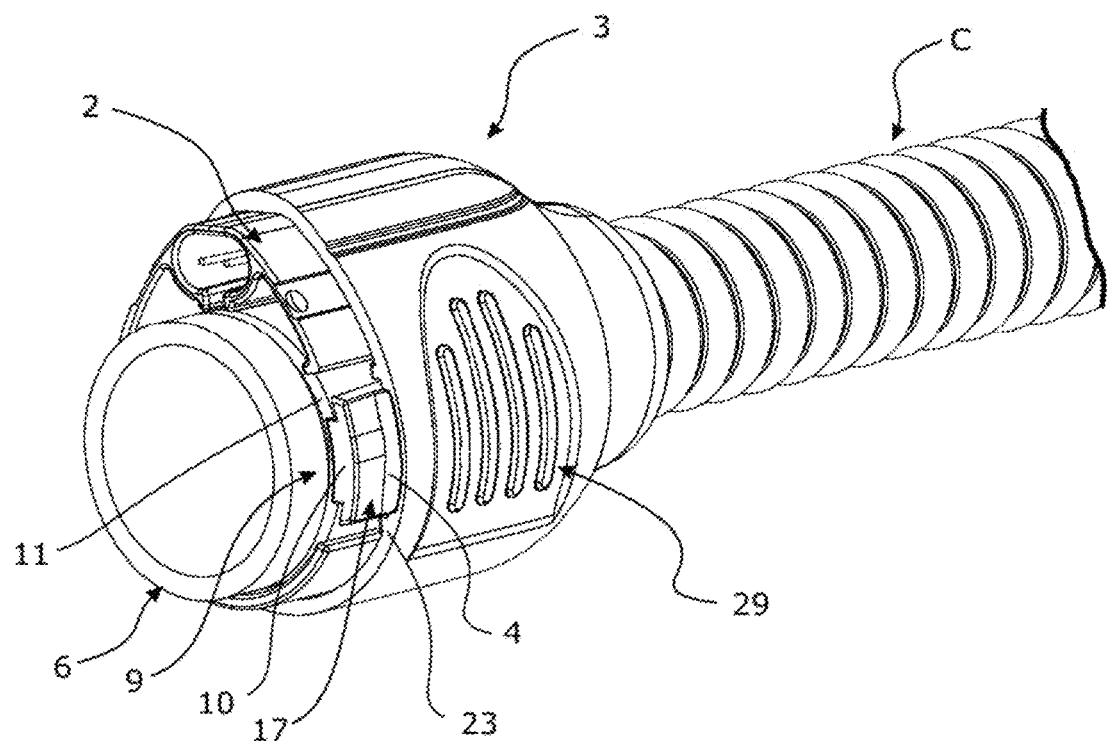
FIG. 4 illustrates an embodiment of a connector, in particular a sequence of a connection in progress being made, where the outer body and the inner body are moved in tandem or together along a shank or shaft of another connector, to move or bring connection features of the connector into suitable proximity with connection features of another connector (for a connection to be correctly made).

FIG. 4 illustrates how, a force applied to the surface relief features 4 by outer body 3 (i.e. due to the resistance to movement of the outer body along the inner body), in turn translates to the movement of both the inner and outer bodies moving or in tandem together along the shank or a shaft portion of another connector, such as a second connector 6. In this manner, connection features 9 of the connector 1 can be brought to bear upon the second connector 6, and can be ultimately moved to engage or latch into a suitable connection feature 11 of a second connector 6.

FIG. 4 also illustrates how in various embodiments latch members 17 having an inwardly orientated or directed raised tab 10, the raised tab 10 (or barb or hook type configuration) can be moved into connection with a recess of another connector.

Figure 5:
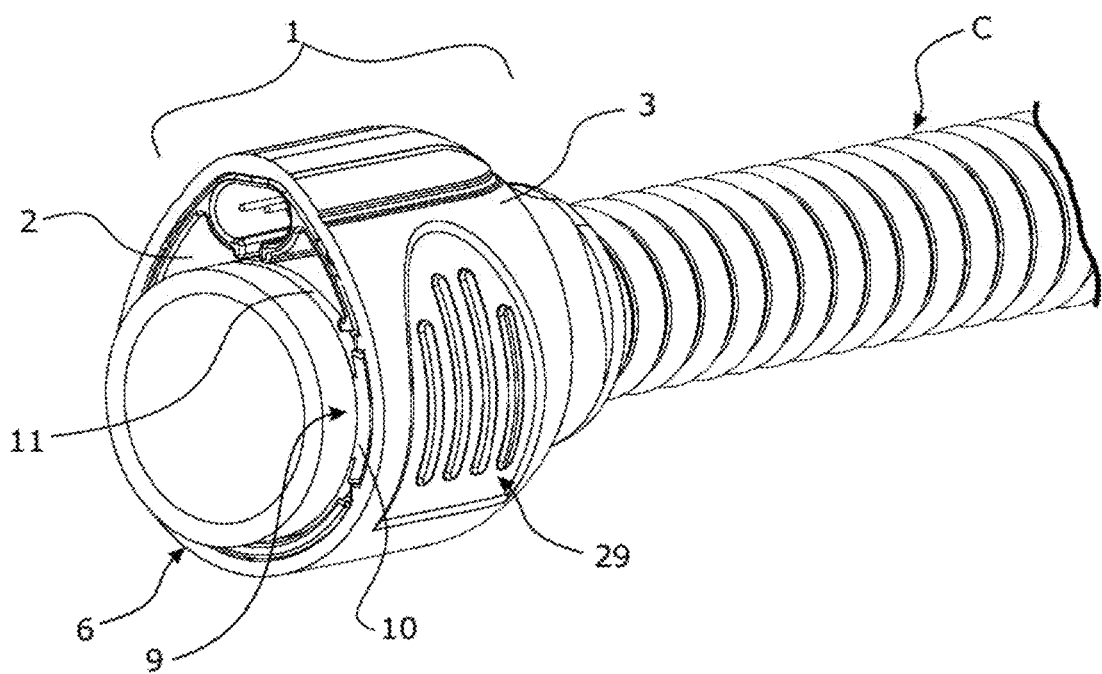
FIG. 5 illustrates a further sequence on from that of FIG. 4 in which an embodiment of a connector has been placed into correct connection with another connector, the connection features of each connector having been mated, and the outer body of the connector having been moved into an operative orientation.

FIG. 5 shows the connector 1 in a connected arrangement with another connector, such as a second connector 6. Note the connection features 9 may have raised tabs 10 of latches 17 are located within the connection feature 11 of the second connector 6. Also note in this embodiment that in this operative orientation of the outer body 3 with respect to the inner body 2, the outer body forms a collar or housing to the inner body 2.

FIGS. 6A-E show a sequence of the connector 1 being put into connection with a second connector 6.

FIG. 6A shows the connector 1 when separate from a second connector 6.

FIG. 6B shows the second connector 6 (e.g. a male connector portion) being placed into the cavity of the female connector portion (e.g. the inner body 2 at least partially receives the second connector 6).

FIG. 6C shows the outer body 3 being moved along the inner body 2, and a surface relief feature 4' of the outer body 3 encountering a surface relief feature 4 of the inner body 2. The surface relief feature 4' may be leading edge 23 or surface. The encountering of such a surface relief feature 4 results in a resistance to the outer body 3 being able to be slid or translated along the inner body 2.

FIG. 6D illustrates how when a user continues to apply a force or sliding pressure to the outer body 3, with sufficient force, the outer body 3 translated the force or pressure to being applied to the inner body 2. In this way, the inner body 2 and the outer body 3 are both moved toward the second connector 6, and the inner body 2 is urged into greater receipt with the second connector 6. Once the user has continued to apply a sufficient force to the outer body (which is translated to the inner body via the surface relief features 4), the connection features 9 of the inner body 2 can be placed into contact or received by the connection feature 11 of a second connector 6, for example a raised tab 10 can be received by a recessed connection feature 11 of the second connector.

FIG. 6E shows how with continued application of a sufficient force or sliding pressure, the resistance created by the interference between surface relief features of the outer and/or inner body 3,2, can be overcome and the outer body 3 can finally be slid or translated home into an operative orientation. In doing so, the outer body 3 may fully house the inner body, and/or can assist with retaining or securing the connection features 9 of the inner body 2 into a retained or secured position or location with the connection features 11 of a second connector 6. The inner body 2 of the connector 1 is now fully housed or surrounded by the outer body 3 (acting as a collar).

FIGS. 7A-E illustrate further embodiments of surface relief features 4, 4' on the outside surface of the inner body 2 and the inside surface of the outer body 3, and how they may be configured for engagement or interference therebetween.

FIGS. 7A-7E illustrate how one or both of the surface relief features 4, 4' of the inner body 2 and the outer body 3 may have a ramped face 24, 26.

Figure 7A:
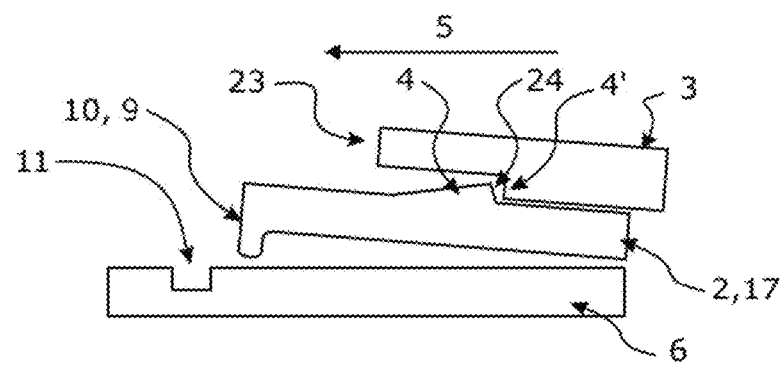
FIGS. 7A-E illustrate further alternative embodiments of surface relief features on the outside surface of the inner body and the inside surface of the outer body, and how they may be configured for engagement or interference therebetween.
Figure 7B:
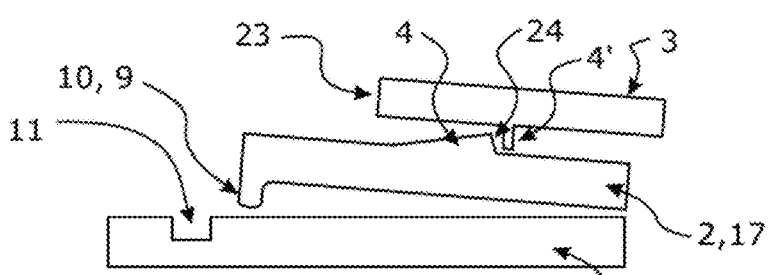
Figure 7C:
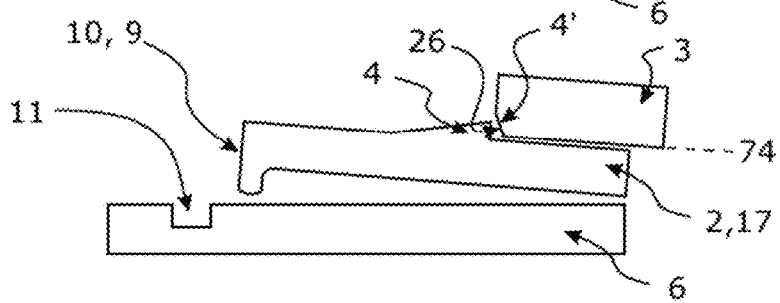
Figure 7D:
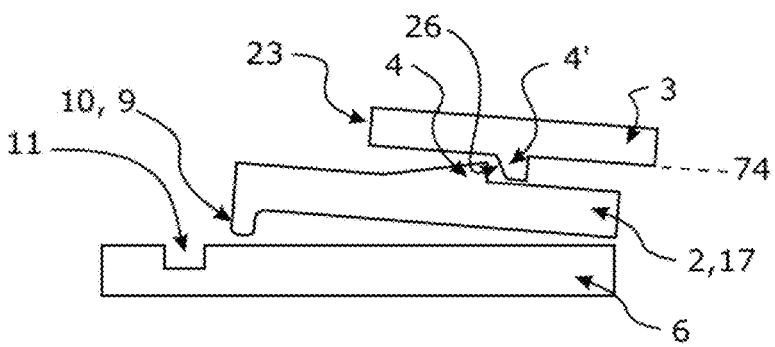
Figure 7E:
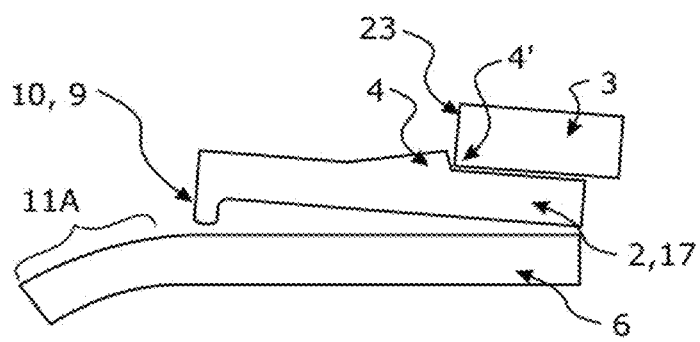

FIGS. 7A, 7B, 7E illustrate how a surface relief feature 4, such as protrusion or raised profile, or leading edge 23, can have a ramped face 24. The ramped face 24 on the inner body 2 is inclined at an angle from the outer surface of the inner body 2 (or may be a latch member 17) to a most radially outward point or height. The angle and direction of the ramp of the inner body of FIGS. 7A, 7B and 7E is more particularly described with reference to FIGS. 10A, 10B.

In FIGS. 7C, 7D the protrusion or raised profile having a ramped face 26 is provided on an inside surface 8 of the outer body 3, while the surface relief feature 4 of the inner body 2 stands or extends substantially without a ramped face—in these configurations, the ramped face inclines at an angle from the inner surface 8 of the outer body to a more radially inward point (or more radially inward height of such a protrusion or profile), and being inclined or inclining in a direction away from the leading edge 23 or face of the outer body 3. Optionally, such a ramped face may be at an angle of about 40° to about 60° (degrees), or could be at an angle of about 45°, or may be at an angle of less than about 90° when said angle is measured with respect to the inner surface of the outer body, and/or an axis 74 coincident or planar with the inner surface of the outer body or, when the angle is measured from an axis perpendicular to the outer surface of a second connector.

FIG. 7E illustrates a further embodiment in which the inner body 2 and the second connector 6 are configured to provide for a frictional or interference-type connection fit. In this embodiment, the inner surface of the inner body 2 can engage with the outer surface of the second connector 6 to retain the inner body 2 relative to the second connector 6. In some configurations the second connector comprises a curved surface 11A. As the outer body 3 is slid from an inoperative orientation to an operative orientation the connection features of the inner body come gradually into greater engagement or fit with the curved surface 11A, and can act to fittingly retain the connection feature 9 upon the surface 11A. It will be appreciated that the frictional or interference-type connection fit as shown in FIG. 7E can be combined with the configuration of the surface relief features 4, 4' as shown in FIGS. 7A-7D.

Figure 8:
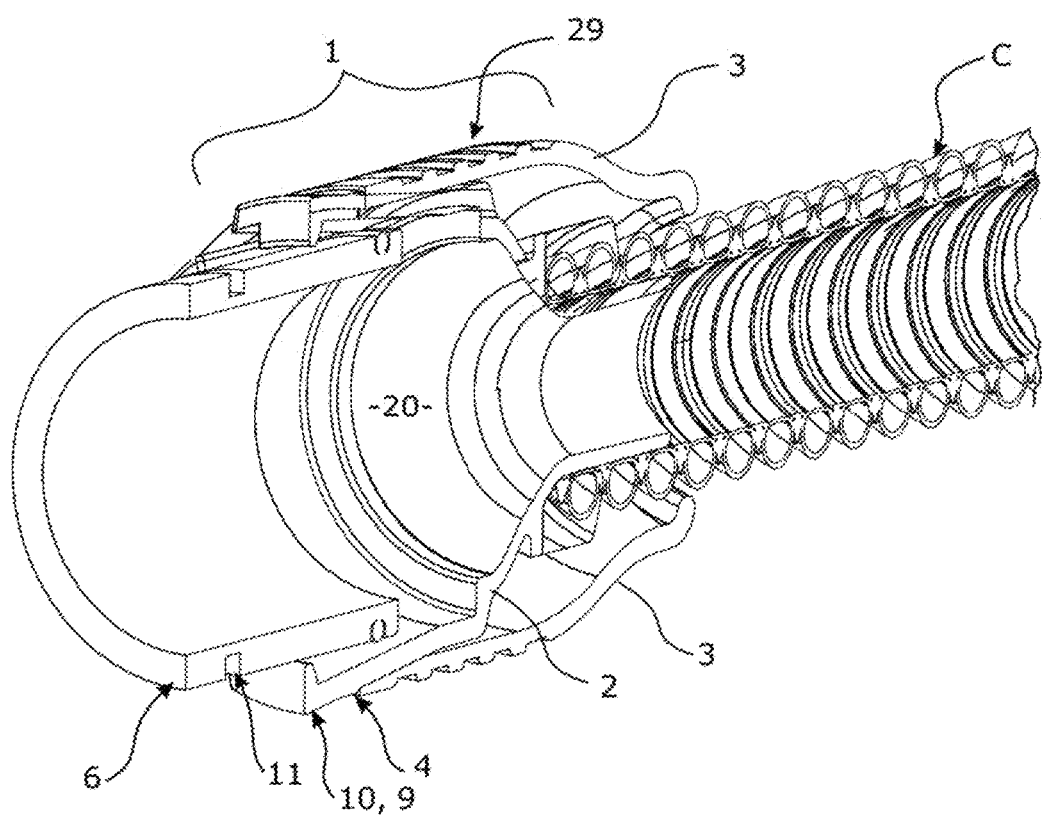
FIG. 8 shows a cross-section through an embodiment connector, such as that of FIGS. 3 and 6C.

FIG. 8 shows a cross-section through a connector 1 which is in progress of being put into connection with a second connector 6, but for which the connection has not yet been completed. The outer body 3 is shown as having its surface relief features (e.g. in this instance a leading edge 23 or leading face of an end of the outer body 3) being in interference or encountering resistance from surface relief features 4 of the inner body 2. FIG. 8 is a cross-sectional view of one embodiment of the sequence shown by FIGS. 3 and 6C.

Provision of the surface relief feature(s) 4 facilitates a first resistance to a force of displacement of the outer body 3 from being slidably moved from the inoperative orientation toward the operative orientation (i.e. in the direction indicated by arrow labelled as item 5). Such a first resistance requires that a force of displacement needed to overcome the first resistance is greater than a force of displacement subsequently required to complete the outer body 3 from being slidably moved past or beyond the surface relief feature(s) 4 and into the operative orientation.

In one embodiment, as the connector 1 is configured to connect to a second connector 6, in use, the force required to engage the inner body 2 with the second connector 6 is less than the force required to move the outer body 3 from the inoperative orientation to the operative orientation.

The difference between the forces required during different stages of connection between the connector 1 and the second connector 6 allow for an overall simplified and staggered connection. In some embodiments, in a first stage of connection the inner body 2 is brought into engagement with the second connector 6. In a second stage of bringing the connector 1 into a connection with the second connector, the outer body 3 is moved from an inoperative orientation (position 60, and including position 61, in FIG. 9A) to an operative orientation (position 62, in FIG. 9B). The force required to complete the first stage of engagement is less than that required to perform the second stage of connection.

To facilitate connection, a user can grip the outer body 3 and align the inner body 2 with the second connector 6. Once the connector 1 is initially brought into engagement with the second connector, the first stage of force is implemented and applied to the outer body 3 by a user—this first stage of force urges the outer body from the retracted or inoperative position along the inner body and towards the operative orientation. A surface relief feature 4' of the outer body, such as leading edge 23 of the outer body 3 contacts at least one of the surface relief features 4 of the inner body 2 (as for example shown in FIG. 6C.) The force required to complete the second stage of connection, is greater than that required to complete the first stage. As the user continues to apply a force to the outer body 3, the outer body 3 moves over the surface relief features (for example of the inner body) and into the operative orientation (as shown for example by FIG. 6E and FIG. 9B.)

Throughout the staged connection of the connector 1 to a second connector 6, the user only has to provide a force to the outer body 3. This can greatly simplify the connection process. In particular, connection can be facilitated using only one hand (i.e. the connection may be made single-handedly). This can leave a user's other hand free to perform other tasks.

As a greater force is required to move the outer body 3 beyond the surface relief feature 4 of the inner body, in applying the first stage of force to the outer body, a user can (in tandem) move the outer body and the inner body together along a shank of a second connector, thereby moving the connection features 9 of the inner body 2 into an alignment position with the second connector. Once the outer body 3 is moved beyond the surface relief feature 4, the outer body 3 the slides along the inner body 2 and acts to preferentially retain the connection features 9 within a connection feature 11 of a second connector. Advantageously, the difference in forces between the two stages can allow the outer body 3 to be prevented from moving to the operative orientation or resistance is provided so as to not allow it to move to the operative orientation before the inner body 2 has successfully made connection to the second connector 6.

Figure 9A:
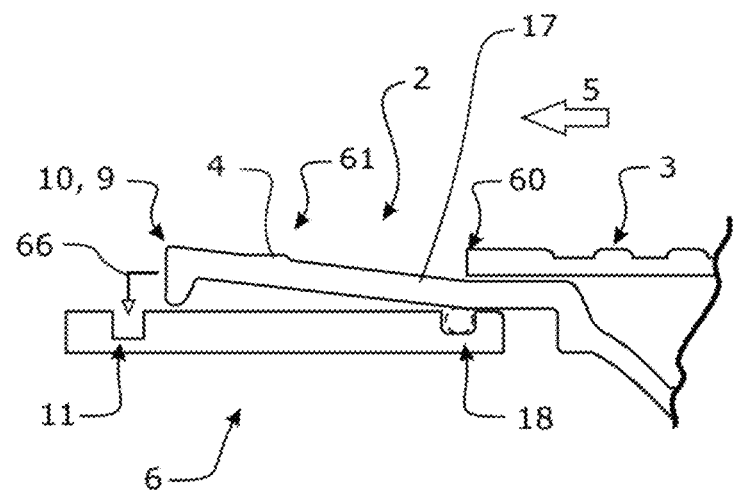
FIGS. 9A-B show a close-up of a part of a connector, in particular how an outer body moves from an inoperative orientation to an operative orientation, and how connection features of an inner body can be moved into alignment with connection features of a second connector, thereby allowing the outer body to be slid into the complete operative orientation.

During the process of connecting the connector 1 with a second connector (such as 6), until the connection features 9 of the inner body 2 are suitably aligned with the connection feature 11 of the second connector 6, the connection features 9 of the inner body 2 and the second connector are not able to engage or be mated with each other (for example as shown in FIG. 9A). This is because the connection features 9 of the inner body 2 are in contact with an outer surface of the second connector 6, and so are physically prevented from being directed out of the pathway along which the outer body 3 wishes to slide in order to reach the operative orientation (as shown by FIG. 9A).

Accordingly, as the connection features 9 of the inner body 2 are prevented from mating with the connection features 11 of the second connector 6, such connection features 9, for example at the end of a latch member 17, are not able to be deflected by the outer body 3 (such as radially inwardly) sufficiently to allow for the outer body 3 to be slid completely to the operative orientation. That is, the connection features 9 themselves contribute to the resistance against being able to slide the outer body 3 along the inner body 2 from the inoperative orientation to the operative orientation. As such, a user sliding the outer body 3 from the inoperative orientation toward the operative orientation encounters a particular resistance.

The resistance allows the force applied by a user to the outer body 3 to be translated or at least in part transferred to the inner body 2 via the engagement of the respective surface relief features 4, 4' of the inner body and outer body. The outer body 3 and inner body 2 are therefore shifted together more toward the second connector for suitable alignment and engagement of the respective connection features (9 of the inner body, and 11 of the second connector).

Figure 9B:
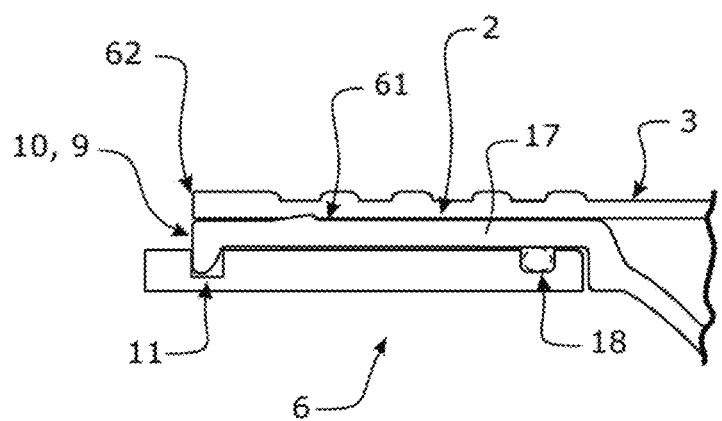

Once the connection features 9, 11 are aligned with each other, they can engage or mate (for example as shown in FIG. 9B). The connection features 9 can then be received by the connection feature 11 of a second connector and move or be deflected inwardly (e.g. radially inwardly by applied force from the inner surface of the outer body 3), and be substantially moved out of the pathway through which the outer body 3 wishes to travel in order to be able to reach the operative orientation (for example the connection feature 9 of the inner body 2 moves along the pathway indicated by arrow 66 into an alignment and is then retained in orientation with the connection feature 11 of a second connector).

Once the connection feature 9 moves into engagement or receipt or is/are mated with the connection feature 11 of the second connector, the resistance to the outer body 3 being slid into the operative orientation is significantly reduced, and the continued application of (a lesser) force by a user allows the outer body 3 to be slid into the operative orientation. In other words, the force required by the user to slid the outer body 3 along the inner body, and to push the outer body 3 and inner body 2 in tandem toward the second connector 6 is greater than the force subsequently required to slide the outer body 3 into the completed operative orientation once the connection features 9 have been moved out of the outer body's pathway of travel.

Accordingly, the connector of this disclosure allows for a user to single-handedly operate the connector 1 and put the connector 1 into a connection with a second connector. Advantageously the mechanisms for enabling such a staged connection process may be concealed when the outer body 3 is in the operative orientation. The user only needs to shift the outer body 3 from the inoperative orientation to the operative orientation and in doing so, the connector automatically provides for a system to improve the likelihood of a correct connection being made.

In particular configurations, when said at least one connection feature 9 of said inner body is in an engagement with a connection feature 11 of a second connector 6, the force required to engage the inner body 2 with the second connector 6 may be less than about 50 Newtons, and in particular may be about 30 Newtons.

In other configurations, when said at least one connection feature 9 of said inner body 2 is out of an engagement with a connection feature 11 of a second connector 6, the force required to move the outer body 3 from the inoperative orientation to the operative orientation may be greater than about 50 Newtons, and in particular may be about 100 Newtons.

In further embodiments, the surface relief feature(s) 4 can be provided about an outer surface 7 of the inner body 2. Optionally, or in addition, surface relief feature(s) can be provided about an inner surface 8 of the outer body 3. In some configurations, one or more surface relief feature(s) may extend(s) as a continuous or discontinuous formation or formations about a complete or a partial circumference of the inner body 2 (i.e. on the outer surface 7) and/or of the outer body 3 (i.e. on the inner surface 8). Still further, at least one of the surface relief features 4 can be a protrusion or protrusions that is/are configured to provide for the aforementioned resistance.

In further embodiments, the connector 1 and/or a second connector 6 to which the connector 1 is to be connected, or both, can comprise of at least one connection feature 9 that is/are configured for retaining the connector 1 in a position relative to a second connector when such a connection is made. For example, such connection features 9 may assist with ensuring a desired axial (i.e. longitudinal) positioning or location of the connector 1 relative to a second connector 6 is made, although in addition to this one or more of the connection features 9 may assist with positioning or locating the connector 1 in a desired radial orientation relative to such a second connector 6.

When the outer body 3 is moved into the operative orientation (e.g. by sliding along the outside surface of the inner body 2), the outer body 3 may be configured in a manner so as to assist with maintaining or securing at least one connection feature 9 into a retained orientation relative to such a second connector 6.

For example, at least one connection feature 9 of the inner body 2 may comprise of a raised tab (identified as item 10). Such a raised tab 10 can extend in a substantially radially inward direction for receipt or engagement with a recess (such as a slot or annular groove labelled as item 11) of a second connector 6. Such a tab 10 can be of hooked or barbed type arrangement for making an engagement with a reciprocally shaped feature on such a second connector 6. It will be appreciated the connection feature 9 with such a raised tab 10 may be reconfigured in a manner, such that the connection feature 9 is sized or shaped or sized and shaped for receipt with the second connector 6.

Further, an inside surface 8 of the outer body 3 may be configured so as to ensure the connection feature(s) 9 of the inner body 2 are held in a retention orientation or position with respect to the second connector 6. In this way, a security or maintenance of the connection between the connection features 9 of the inner body 2 with the connection feature indicated as item 11 of the second body 6 can be facilitated.

Accordingly, an inside surface 8 of the outer body 3 may assist with a radially inward deflection of one or more of the connection features 9 of the inner body 2. In this manner, the aforementioned security or maintenance of connection of the inner body 2 with a second connector can be facilitated.

In some configurations, the inner body 2 may have one or more latch members 17. Latch members 17 can be in the form of one or more fingers.

A latch member 17 is advantageously a deflectable portion of the inner body 2. For example, a latch member 17 may be deflectable substantially radially inwardly toward a connection feature 11 of a second connector 6 to which the latch member 17 is to be engaged thereto when the outer body 3 is moved or slid into the operative orientation. A latch member 17 may formed so as to be of an outwardly flared orientation or may be suitably shaped, so that upon contact or engagement by an inner surface 8 of the outer body 3 (e.g. when the outer body 3 is moved into the operative orientation), the latch members 17 may be deflected or moved or bent substantially radially inwardly (for example into a latching or latched orientation or position with a connection feature 11 of a second connector 6). An end of a latch member 17 can be provided with the connection feature 9 which can include the raised tab 10.

Where the connection feature 9 of at least one of the one or more latch members 17 has a raised tab 10, such a raised tab 10 (or a barb or hook type arrangement) is configured to be received by a connection feature (e.g. a recess or groove) of a second connector 6. In particular, such a connection can be made when the raised tab 10 (or other shaped feature such as a barb or hook) is suitably aligned or oriented for engagement (e.g. when aligned for engagement with the connection feature 11 of the second connector 6).

In an alternative, the connection feature 9 of one or more of the latch members 17 could be provided as or with a recess for receipt of a connection feature of a second connector, such a connection feature of the second connector could be a raised tab or a barbed or hook type arrangement for receipt by the recess or a windowed type portion of the connection feature 9 of the inner body 2. Again, such a connection can be made when the connection features of the inner body and the second connector are suitably aligned or oriented.

An outside surface of one or each of the latch members 17 is typically the same outside surface 7 as that of the inner body 2. Such an outside surface of a latch member can be provided with the surface relief feature(s) 4.

The outside surface 7 of the inner body 2 may optionally include one or more longitudinally orientated channels or recesses or slits or slots which may at least in part act as a guide path 12 for a guide path locator 13. Alternatively, it may be an inside surface of the outer body 3 that has such channels or recesses or slits or slots acting as a guide path, and in this arrangement, the inner body 2 would then be provided with a guide path locator. Such a guide path 12 and a guide path locator 13 providing for an orientation of the inner body with respect to the outer body, and for guiding the outer body 3 in a preferred direction of travel when being moved between the inoperative and the operative orientations.

The guide path 12 may transition or taper from a larger width at the base of the inner body 2 to a smaller width at the terminal end of the guide path 12. The guide path 12 and guide path locator 13 may provide for a maximum retraction position of the outer body 3 relative to the inner body 2. The maximum retraction position being reached when the guide path locator 13 of the outer body 3 comes into engagement with the terminal end of the guide path 12 of the inner body 2. In this way, the base of the guide path may act as a stop to the guide path locator.

In further embodiments, when the outer body 3 is in a maximum or fully retracted position (i.e. the inoperative orientation), the movement of the latches 17 are not, at least to an extent, restricted by the outer body 3. In this way, the latches 17 may be allowed to flare outwardly back to their original position. When the outer body 3 is in a fully retracted position, the latches 17 may be self-disengaging from the second connector 6 or from a connection feature 11 of the second connector 6, or are free to return to their initial position.

In some embodiments the latch members may be flared outwardly to provide for an effective sized mouth of the inner body to allow for receipt by the inner body 2 of the second connector 6, in particular when the latch members or connection features are in their inoperative orientation or position.

Figure 10A:
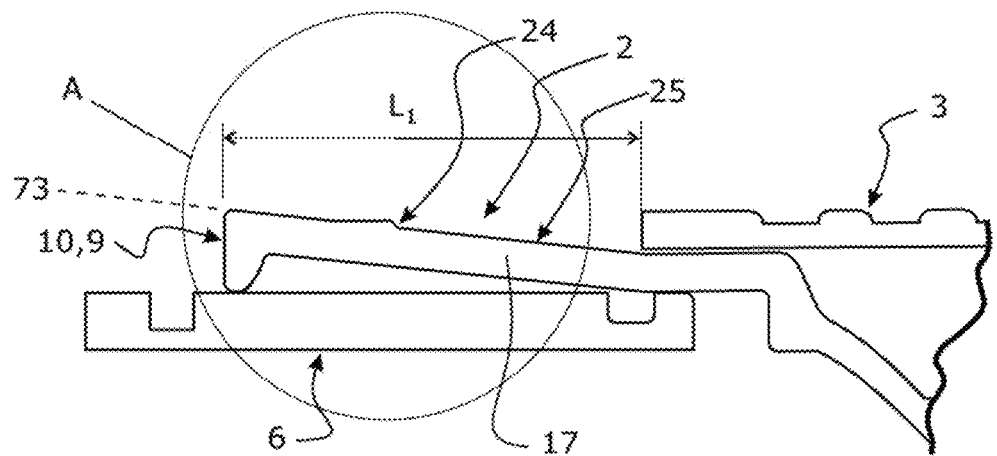
FIG. 10A shows a cross section of a second connector, inner body and outer body.
Figure 10B:
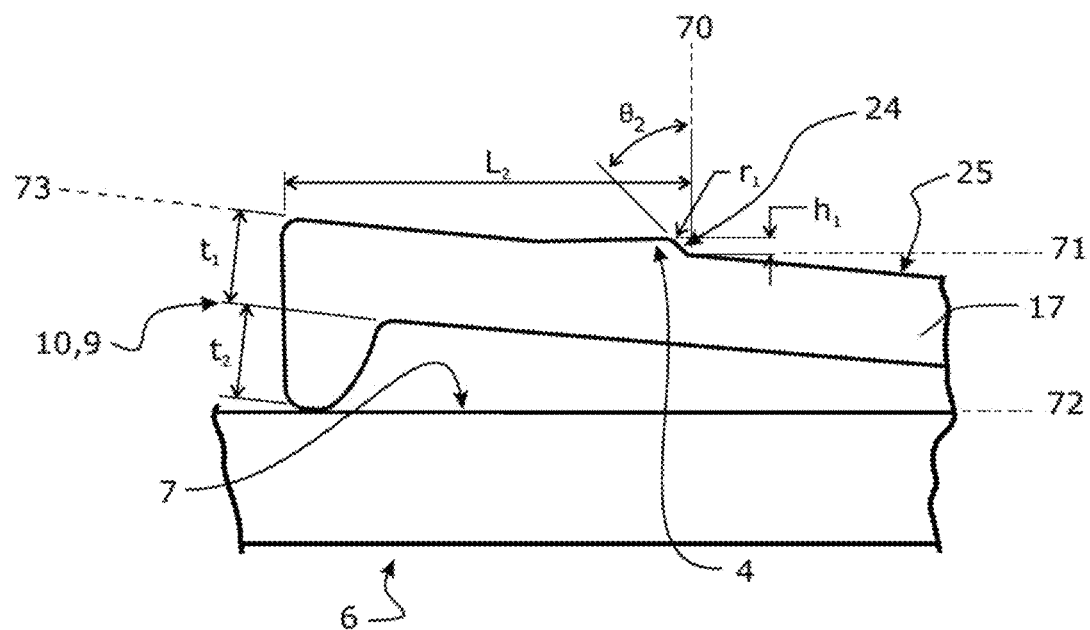
FIG. 10B is a close-up view of the region indicated as item A in FIG. 10A, FIG. 10B illustrating details of particular angles and dimensions for a surface relief feature upon a latch member and of a connection feature of an inner body.

FIG. 9A shows a latch member 17, the latch member may be sufficiently outwardly flared so as to not initially engage with the outer surface of the second connector 6. The outward flare of the latch member provides for easier receipt of the second connector 6 by the inner body 2. As the outer body 3 moves in the direction 5 from an inoperative position to an operative position the latch member may be deflected or moved or bent substantially radially inwardly. FIGS. 10A, 10B show where a latch member 17 is flared outward to a degree such that during initial engagement between the inner body 2 and the second connector 6, the latch member and/or a connection feature 9 is/are in contact with the outer surface of the second connector 6.

In still further embodiments, optionally the outside surface 7 of the inner body 2 may optionally include one or more projection or recess features 14 to engage with or be received by a reciprocally shaped feature 15 on an inside surface 8 of the outer body 3, which are engageable with each other when the outer body 3 and the inner body 2 are orientated with respect to each other in the operative orientation (i.e. when the outer body 3 has been slid along the inner body and moved into the correct and desired operative orientation). The one or more projection or recess features 14 and reciprocally shaped feature 15 may provide a retention or resistance force to movement of the outer body 3 relative to the inner body 2 once the outer body 3 is in the full operative orientation or the complete inoperative orientation. The retention or resistance force being overcome by movement of the outer body 3 from or to an operative or inoperative orientation.

Such features (items 14, 15) may optionally provide a facility for some form of haptic feedback (e.g. a 'click' noise or a click-in or snap type fit) for a user to confirm the correct engagement of the outer body 3 with the inner body. While these features are useful, they do not in themselves provide feedback to a user to confirm the correct engagement of the connector 1 with a second connector 6.

Accordingly, in further embodiments, the connector 1 of this disclosure is configured so that a force required to move the outer body 3 to the operative orientation when the at least one connection feature 9 of the connector 1 and/or of the second connector 6 are aligned for an engagement with each other into a or their retained orientation, is less than a force required to move the outer body to the operative orientation when the connector 1 and the second connector 6 are attached to each other yet the connection features 9 of the connector 1 and/or the second connector 6 are out of alignment or are not oriented for an engagement with each other into their correct or desired retained orientation.

In particular, in some configurations of the above embodiment, the force required to move the outer body 3 to the operative orientation when the connection features 9 of the connector 1 and/or of the second connector 6 are aligned for an engagement with each other into a retained orientation is less than about 50 Newtons, and may advantageously be less than about 30 Newtons.

In particular, in some configurations of the above embodiment, the force required to move the outer body 3 to the operative orientation when the connector 1 and the second connector 6 are attached to each other, yet the connection features 9 of the connector 1 and/or the second connector 6 are out of a suitable alignment for an engagement with each other into a retained orientation, is greater than about 50 Newtons, and may advantageously be about 100 Newtons.

Various configurations between the inner body 2 and the outer body 3 of the connector 1 are contemplated for facilitating an outer body which encounters a resistance when moving from the inoperative orientation (i.e. a "retracted" collar position) to the operative orientation (i.e. an "extended" collar position). It is the level of resistance to movement that determines the actual force required to overcome the resistance that is encountered. However, it will be appreciated that the provision of surface relief features 4, 4' on either or both of the inside surface of the outer body 3 or the outside surface of the inner body 2 and their respective contact and engagement helps govern the force needed to overcome the resistance, and allow the outer body 3 (or the inside surface 8 of the outer body 3) to be moved beyond the initial point of resistance and into the operative orientation.

As shown by the figures, in particular embodiments the surface relief feature 4 on an outside surface of a latch member 17 can be a protrusion or a raised profile that extends outwardly (i.e. radially outwardly) from the outside surface of the inner body or the latch member.

Such a protrusion or raised profile can be positioned or located substantially a predetermined length from an end 16 of the latch member 17. The end 16 is the end of the latch member 17 toward which the outer body 3 is moved toward when being moved into the operative orientation.

FIG. 10A illustrates a cross-section of a second connector 6, inner body 2 and outer body 3, with an added reference dimension L1. L1 shows the length of the latch member. FIG. 10B shows an area A of the cross section of FIG. 10A with indicative axes 70, 71 and 72 shown. Axis 72 is coincident with the surface 7, located on the outer surface of the second connector 6. Axis 71 is parallel to axis 72 but vertically offset. Axis 70 is an axis perpendicular to both axis 71 and axis 72, and passing through the point where the latch member transitions into surface relief feature 4. The dimension L2 indicates the distance of a surface relief feature 4 from the terminal end of the latch member. The dimension t1 indicates the thickness of the latch member. The dimension t2 indicates the thickness of the connection feature 9, or the raised tab 10. Angle θ2 defines the angle of a ramped face of the surface relief feature 4 with respect to the axis 70. The dimension h1 indicates the height of the top of the ramped face of the surface relief feature 4 relative to axis 71. Radius r1 corresponds to the radius of the round at the top of the ramped surface.

In some embodiments the dimensions as shown in FIGS. 10A and 10B may instead be referenced to other parts of the inner body 2 such as the outer surface of the latch member. In these embodiments the dimensions may be independent of the position of the latch.

The ratio between the height of the ramped surface h1 and the thickness of the connection feature t2 (h1:t2) may be about 5:100 to about 5:1, optionally between about 5:50 to about 5:1.5, optionally between about 5:10 and about 5:2, optionally between about 5:1 and 2.5:1, and optionally between about 1.6:1 and 2:1. Optionally, the ratio h1:t2 is about 1.8:1. Optionally the height of the ramped surface is between about 5% and about 500% of the thickness of the connection feature, optionally between about 7.5% and 250%, optionally between about 10% and 100%, optionally between about 15% and about 30%, and optionally between about 18% and about 23%. Optionally the height of the ramped surface is about 20% of the thickness of the connection feature.

Such a surface relief feature, for example a protrusion or raised profile, can be positioned or located about 0 mm (i.e. at the terminal end) to about 15 mm from the terminal end 16 of the latch member 17, optionally between about 3 mm and about 10 mm, optionally between about 5 mm and about 8 mm, and optionally between about 6 mm and about 8 mm. Optionally, the protrusion or raised profile, can be located about 7 mm from the end 16.

Such a protrusion or raised profile can have a ramped face 24 as shown in FIGS. 10A and 10B. The ramped face 24 being inclined at an angle from the outer surface 25 of the latch member 17 to a most radially outward point or height, and being inclined (or including) in a direction toward the end 16 of the latch member 17 (i.e. inclining in a direction toward the end of the latch member to which the outer body is moved toward for the operative orientation). Optionally, such a ramped face can be at an angle of about 40° to about 60° (degrees), though may alternatively be at an angle of about 45°, or the angle may be less than about 90° when the angle is measured with respect to the outer surface 25 of the latch member 25, and/or an axis 73 coincident or planar with the outer surface 25 of the latch member 17.

Optionally, the angle of the ramped face may instead be provided at an angle which is measured from an axis 70 perpendicular to an axis 72 coincident with the outer surface of the second connector 6 (as shown by the angle θ2). Optionally, such a ramped face can be at an angle (θ2) of about 40° to about 60° (degrees), though may alternatively be at an angle (θ2) of about 45°, or the angle (θ2) may be less than about 90° when the angle is measured from an axis perpendicular to the outer surface of a second connector.

Accordingly, in one embodiment, the surface relief feature 4 on the outside surface of the latch member 17 is provided to interfere with, or be contacted by, a surface of the outer body 3 when the outer body is being moved in a direction from the inoperative orientation toward the operative orientation.

In various configurations of the above embodiment, the surface relief 4' feature of the outer body 3 can be a leading edge 23 or face of the outer body. For example, the leading edge or face could be an end edge or an end face of the outer body 3 that makes initial interference or contact with the surface relief feature 4 provided on the outside surface of the latch member 17 or of the inner body 2 when the outer body is being moved in a direction of travel 5 from the inoperative orientation to the operative orientation. In addition, or alternatively, it is an inside surface 8 of the outer body 3 that can comprise of one or more of the surface relief features 4', a leading edge or face of which would be configured to make an initial interference or contact with a surface relief feature 4 of an outside surface of the inner body 2.

Figure 11:
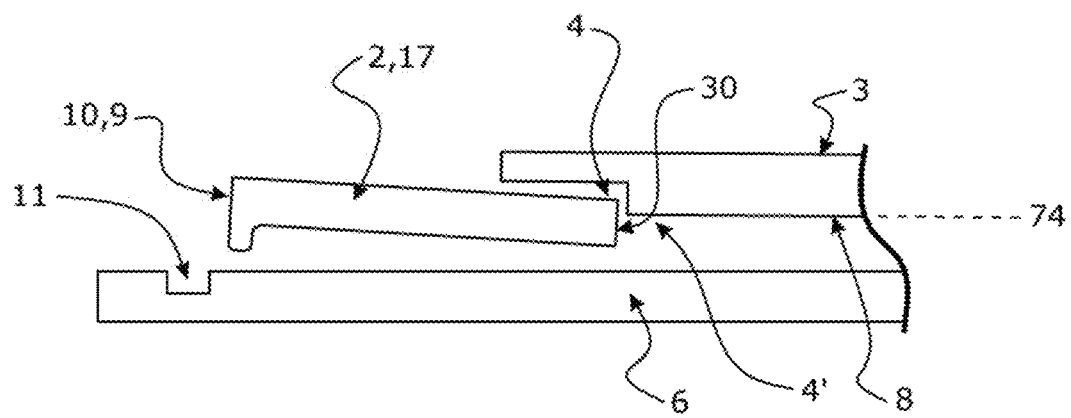
FIG. 11 shows a cross-section of an embodiment of a connector.

In an embodiment as shown in FIG. 11, when the outer body 3 is in the inoperative orientation, the outer body 3 may be sufficiently retracted from the inner body, so that a surface relief feature on the inside surface 8 of the outer body 3 is removed from being in contact with the outside surface of the inner body. Accordingly, in such a configuration, when the outer body 3 is being moved from this retracted position to the operative orientation, such a surface relief feature (e.g. a bump or projection or other formation provided about the inside surface 8 of the outer body 3) can then engage or make an interference contact with a leading edge 30 or end face of the inner body. In this manner, an outside surface of the inner body 2 does not need to be provided with a surface relief feature. As such, either an inside surface of the outer body or an outside surface of the inner body, or both such surfaces, may be provided with suitable surface relief features.

In one embodiment, one or more of the surface relief features 4' on the inside surface 8 of the outer body 3 may be a protrusion or a raised profile that extends inwardly (e.g. substantially radially inwardly) from the inside surface. Optionally, such a protrusion, or raised profile, or leading edge 23 of the outer body 3 can have a ramped face. Such a ramped face inclining at an angle from the inner surface 8 of the outer body to a most radially inward point (or more radially inward height of such a protrusion or profile), and being inclined or inclining in a direction away from the leading edge 23 or face of the outer body 3. Optionally, such a ramped face may be at an angle of about 40° to about 60° (degrees), or could be at an angle of about 45°, or may be at an angle of less than about 90° when said angle is measured with respect to the inner surface 8 of the outer body 3, and/or an axis 74 coincident or planar with the inner surface 8 of the outer body 3 or, when the angle is measured from an axis perpendicular to the outer surface of a second connector.

According to the disclosure herein, when in the inoperative orientation, the outer body 3 and the inner body 2 are out of an engagement or association with each other. In this condition, the surface relief features of the inner body or the outer body (or both in situations where they both have such surface relief features) are disengaged or are not in interference with each other (and the outer body has been retracted to the inoperative orientation).

According to the disclosure herein, when in the operative orientation, the surface relief feature 4, 4' of either or both of the inner body 2 and/or the outer body 3 have been put into interference and contact has been made. In addition, a user has had to provide sufficient force to translate or move (e.g. by sliding) the outer body along the (or a) length of the inner body, overcoming the resistance which resulted from the surface relief features providing a resistance, and the outer body being urged into the operative orientation. The user has had to apply an initial force to move the outer body 3 along the inner body 2, and to overcome the resistance to such a sliding or translation by the surface relief features 4, 4'. Once the resistance has been overcome, a user is then able to more easily continue to slide to translate the outer body 3 into the final operative orientation.

When in the operative orientation, advantageously the outer body 3 is configured to urge one or more connection features (or one or more latch members 17) of the inner body 2 inwardly toward a latched configuration with a connection feature 11 of a second connector 6. In addition, in the operative condition, the outer body 3 can maintain or secure the connection features 9 (or one or more latch members 17) of the inner body 2 in a retained orientation relative to a second connector 6; yet when in the inoperative condition, the outer body 3 does not maintain or secure such connection features 9 (or the one or more latch members 17) of the inner body 2 in a retained orientation relative to a second connector 6.

According to the disclosure herein, the inner body 2 defines internally a lumen or gas flow passage 20 for the transport of gas. The outer body 3 provides a housing into which the inner body 2 may be housed. In some embodiments, in an inoperative orientation, the outer body 3 may house a portion of the inner body 2. In an operative orientation the outer body 3 may house a substantial portion of, or a majority of, or the entirety of the inner body 2.

As shown in FIGS. 1-6E the outer body 3 can provide a grip comprising gripping features 29 for a user to more easily hold and thereby actuate connection and may also provide for an aesthetic cover for the inner body 2. The gripping features 29 may comprise a plurality of ribs. The inner body 2 facilitates for a pneumatic connection to be made with another component, for example such as a conduit C, for example as shown in FIG. 8. The inner body 2 of the connecter may be connectable or attachable to a conduit C. Optionally, the conduit may be a medical breathing tube. The inner body 2 may provide for a lumen to provide a gases transport pathway to the lumen of the conduit C.

When in the inoperative orientation, the outer body may be in a retracted position relative to the inner body. Additionally or alternatively, in the inoperative or retracted portion the outer body is allowed to slide over the outside of the conduit which is attached to the lumen of the inner body.

In the various embodiments and configurations described herein, when the connector 1 is connected in a retained orientation with a second connector 6, a pneumatic connection can be made between them.

In particular, the inner body 2 of the connector 1 described herein can be configured so as to be provided as a female connector portion for receiving a male connector portion of another component, such as a male connector portion of a second connector 6.

Still further, according to the above disclosure, the connector 1 can be provided as a component of a medical breathing circuit (such as, but not limited to, a humidified gases delivery breathing circuit, but may additionally include circuits for delivery of anaesthetic or other gases to a patient or user of such a circuit). The connector 1 provides for a female connector portion. The female connector portion is arranged as an inner body 2 and an outer body 3. The outer body 3 can be configured to be in a slidable (or longitudinally translatable) relationship with or along the inner body 2. At least one, or both of, an outside surface of the inner body 2 and an inside surface 8 of the outer body 3 may comprise of surface relief feature(s) 4, 4'. According to this embodiment, the various embodiments, features and configurations as previously described may be provided.

In particular however, the connector of the embodiment described above is adapted for connection with a male end of a second connector 6.

Further, the inner body 2 is an inner connector body, while the outer body 3 is provided as an outer collar body.

According to the various disclosures herein, the connector 1 can be provided with suitably shaped portions or other arrangements for electrical connections to be made, for example in the region indicated as 21. The electrical connections 21 may provide for an electrical connection to heater wires as part of the conduit C. For example, heater wires can provide for a powered heated breathing conduit.

In addition, an outside surface 22 of the outer body 3 can be provided with finger grips or other features for improving the grip or grasp of the connector by a user with their fingers.

Figure 12:
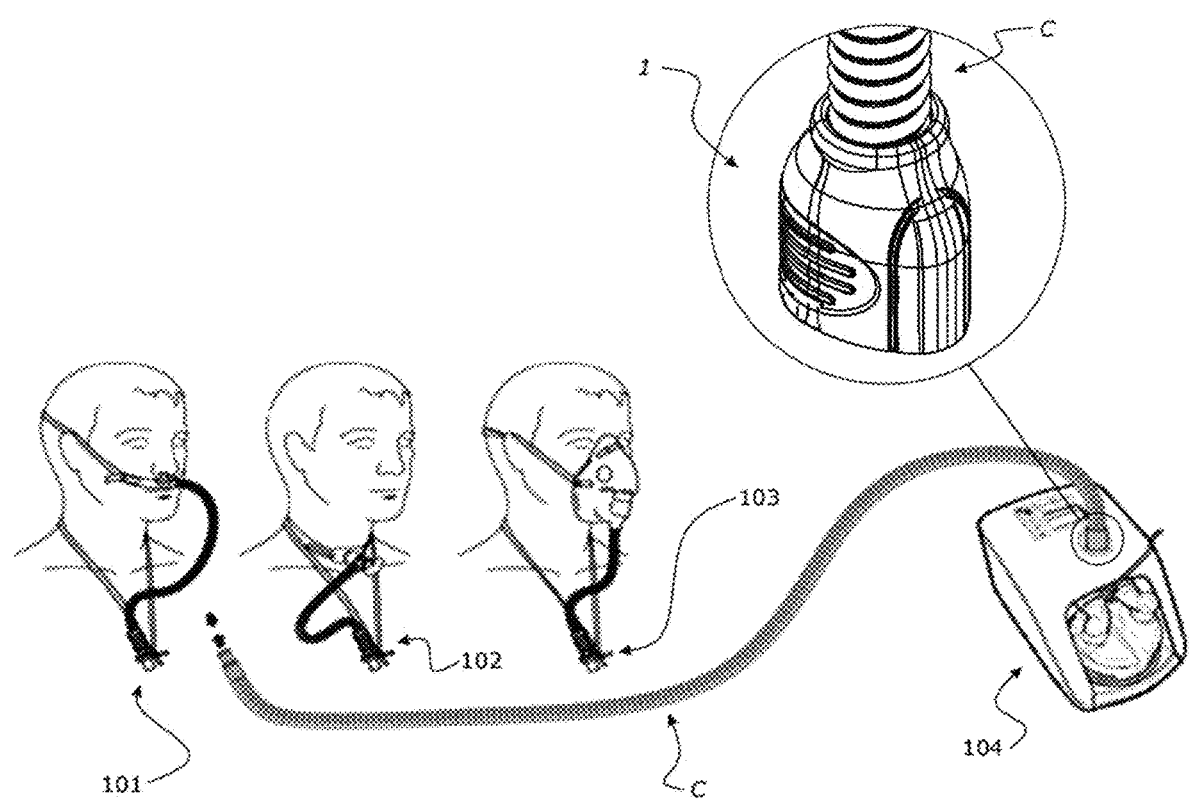
FIG. 12 shows the connector as part of a system to deliver breathing gases to a user.

FIG. 12 shows the connector 1 as part of a system to deliver breathing gases to a user. The connector 1 is connected to a medical breathing apparatus 10. The medical breathing apparatus 104 may be a flow generator integrated with a humidifier, as shown in FIG. 12. Alternatively could be a standalone humidifier, or a standalone flow generator. The medical breathing apparatus 104 comprises a second connector which connects with connector 1. The medical breathing apparatus 104 provides gases along conduit C to a patient interface. The patient interface may be one or a: nasal cannula 101, tracheostomy interface 102, or an oral mask, oral-nasal 103 or nasal mask.

Figure 12A:
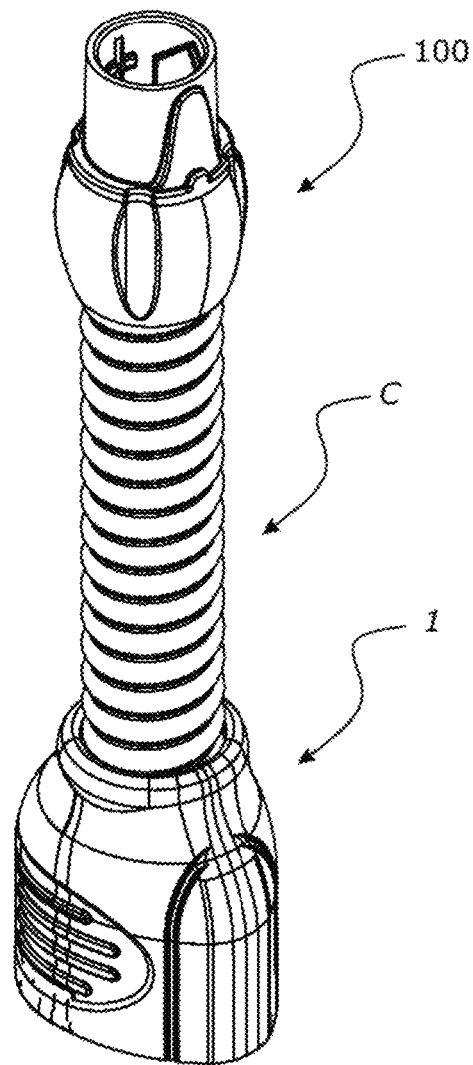
FIG. 12A shows the connector as part of a medical breathing conduit.

FIG. 12A show the connector 1 as part of a medical breathing conduit C. The medical breathing conduit C comprises another connector 100, the another connector may be connectable to a patient interface. The another connector may be a connector as described by unpublished PCT application PCT/IB2016/055258, the contents of which are hereby incorporated by reference in their entirety.

The another connector as described by unpublished PCT application PCT/IB2016/055258 may be provided at one end or a terminal end of a conduit, with the connector as described herein provide at the other end of the conduit. Optionally, the connected described herein is provide at a machine end of a conduit, while the another connector is provided at a patient end of the conduit.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "(s)" following a noun means the plural and/or singular form of that noun.

As used herein the term "and/or" means "and" or "or", or where the context allows both.

Where the terminology "configured to" is used herein, that terminology could alternatively be replaced with "arranged to" or "adapted to".

Where, in the foregoing description reference has been made to integers or components having known equivalents thereof, those integers are herein incorporated as if individually set forth.

The disclosure may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that prior art forms part of the common general knowledge in the field of endeavour in any country in the world.

Certain features, aspects and advantages of some configurations of the present disclosure have been described with reference to use of the gas humidification system with a respiratory therapy system. However, certain features, aspects and advantages of the use of the gas humidification system as described may be advantageously be used with other therapeutic or non-therapeutic systems requiring the humidification of gases or even non-humidified systems. Certain features, aspects and advantages of the methods and apparatus of the present disclosure may be equally applied to connectors and usage with other systems requiring alternative connectors.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Features from any of the configurations describe above may be combined with each other and/or a respiratory support system or humidifier or other components or devices forming a part of a respiratory therapy system or a system for delivery for gases to a patient may comprise one or more of the above described configurations. Moreover, not all of the features, aspects and advantages are necessarily required to practice the present disclosure. Accordingly, the scope of the present disclosure is intended to be defined only by the claims that follow.

The invention claimed is:

1. A system for respiratory therapy comprising:
a conduit with a first connector; and
a medical breathing apparatus comprising a flow generator or a humidifier with a second connector,
wherein one of the first connector or the second connector comprises an inner body and outer body,
the outer body configured to be slidable along the inner body between an inoperative orientation and an operative orientation, the outer body and the inner body being engaged when the outer body is in the operative orientation, the outer body and the inner body being disengaged from each other when the outer body is in the inoperative orientation,
wherein the inner body comprises a surface relief feature configured to provide a resistance to linear movement of the outer body with respect to the inner body to enable engagement of the first connector with the second connector in the operative orientation,
wherein the outer body is configured to overcome the resistance when a linear force is applied to the outer body,
wherein the medical breathing apparatus provides gases to a patient interface, wherein the patient interface is one of a nasal cannula, a tracheostomy interface, an oral mask, an oral-nasal mask, or a nasal mask.

2. The system of claim 1, wherein the inner body comprises a connection feature for retaining the engagement of the first connector with the second connector.

3. The system of claim 2, wherein in the operative orientation, the outer body secures the connection feature in a retained orientation relative to the second connector.

4. The system of claim 2, wherein the outer body is configured to fully house the connection feature of the inner body in the operative orientation.

5. The system of claim 4, wherein the outer body is configured to retain the connection feature of the inner body in a recess of the second connector in the operative orientation.

6. The system of claim 2, wherein the connection feature is a raised tab or protrusion.

7. The system of claim 2, wherein the connection feature is a recess.

8. The system of claim 1, wherein a second force required to engage the inner body with the second connector is less than the linear force.

9. The system of claim 1, wherein a first linear force required to move the outer body from the inoperative orientation to the operative orientation when the inner body is engaged with the second connector is less than a second linear force required to move the outer body from the inoperative orientation to the operative orientation when the inner body is disengaged from the second connector.

10. The system of claim 1, wherein the inner body further comprises a latch member that deflects as the outer body moves from the inoperative orientation to the operative orientation.

11. The system of claim 1, wherein engagement of the first connector with the second connector comprises an electrical connection.

12. The system of claim 11, wherein the conduit comprises a heater wire, and wherein the electrical connection provides power to the heater wire.

13. The system of claim 1, wherein the conduit comprises a third connector for connection to the patient interface.

14. The system of claim 1, wherein the outer body is a female connector.

15. The system of claim 1, wherein the outer body is configured to fully house the inner body in the operative orientation.

* * * * *